United States Patent [19]

Stetter et al.

[11] Patent Number: 5,580,843
[45] Date of Patent: Dec. 3, 1996

[54] SUBSTITUTED 1-ARYLPYRAZOLES

[75] Inventors: Jörg Stetter, Wuppertal; Bernd Alig, Königswinter; Stefan Böhm, Krefeld; Achim Bertsch, Köln; Pieter Ooms, Krefeld; Christoph Erdelen; Jürgen Hartwig, both of Leichlingen; Ulrike Wachendorff-Neumann, Monheim; Andreas Turberg, Erkrath; Norbert Mencke, Leverkusen, all of Germany

[73] Assignee: Bayer Aktiengesellschaft, Leverkusen, Germany

[21] Appl. No.: 356,824

[22] Filed: Dec. 15, 1994

[30] Foreign Application Priority Data

Dec. 22, 1993 [DE] Germany ............... 43 43 832.6

[51] Int. Cl.$^6$ .................... A01N 43/40; A01N 43/56; C07D 401/04; C07D 231/44
[52] U.S. Cl. .................. 514/341; 546/276.1; 546/256; 548/364.1; 548/367.7; 548/368.4; 514/407; 514/404
[58] Field of Search ............... 548/364.1, 367.7, 548/368.4; 514/341, 407; 504/253, 282; 546/279

[56] References Cited

U.S. PATENT DOCUMENTS 5,232,940  8/1993  Hatton et al. ................... 514/407

FOREIGN PATENT DOCUMENTS

| | | |
|---|---|---|
| 201852 | 5/1986 | European Pat. Off. . |
| 301338 | 7/1988 | European Pat. Off. . |
| 301339 | 7/1988 | European Pat. Off. . |
| 295117 | 12/1988 | European Pat. Off. . |
| 352944 | 1/1990 | European Pat. Off. . |
| 374061 | 6/1990 | European Pat. Off. . |
| 3602728 | 11/1986 | Germany . |

OTHER PUBLICATIONS

Journal of the Chemical Society, Perkin Transactions 2, 1993.
Chemical Abstracts, vol. 62, Jun. 7, 1965, No. 12.

*Primary Examiner*—Johann Richter
*Assistant Examiner*—Laura R. Cross
*Attorney, Agent, or Firm*—Sprung Horn Kramer & Woods

[57] ABSTRACT

The invention relates to new substituted 1-arylpyrazoles of the general formula (I)

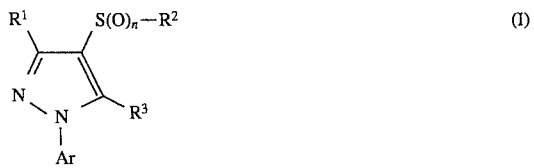

to a plurality of processes for their preparation, and to their use as pesticides.

19 Claims, No Drawings

SUBSTITUTED 1-ARYLPYRAZOLES

The invention relates to new substituted 1-arylpyrazoles, to a plurality of processes for their preparation, and to their use as pesticides.

It has already been disclosed that certain substituted 1-arylpyrazoles, such as, for example, 5-amino-1-[2,6-dichloro-4-(trifluoromethyl)-phenyl]-3-cyano-4-[(trifluoromethyl)-sulphinyl]-1H-pyrazole, have a good activity against pests (cf. for example EP-A 295 117 and EP-A 352 944).

Moreover, a large number of substituted 1-arylpyrazoles are described which can be employed for combating pests (cf. for example EP-A 201 852, EP-A 418 016).

In addition, substituted 1-arylpyrazoles are also used as intermediates for the preparation of pesticides (cf. for example EP-A 301 338, EP-A 301 339, EP-A 374 061, EP-A 260 521).

However, the level and duration of action of the previously known compounds is not entirely satisfactory in all fields of application, in particular in the case of certain insects or when low application concentrations are used.

New substituted 1-arylpyrazoles of the general formula (I)

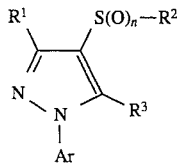

in which
R$^1$ represents hydrogen, cyano, alkyl, alkoxyalkyl, alkylthioalkyl, halogenoalkyl or cyanoalkyl, R$^2$ represents difluoroethyl or trifluoroethyl, R$^3$ represents hydrogen, amino, halogen or one of the following groups

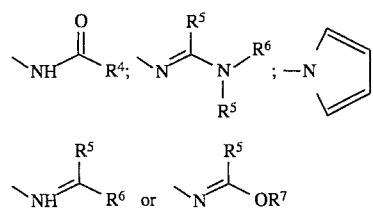

in which
R$^4$ represents alkyl, halogenoalkyl, alkoxyalkyl or optionally substituted phenyl, R$^5$ represents hydrogen or alkyl, R$^6$ represents hydrogen, alkyl or optionally substituted phenyl and R$^7$ represents alkyl or R$^5$ and R$^6$ together with the carbon atom to which they are bonded represent an optionally substituted heterocycle, Ar represents optionally substituted phenyl or pyridyl and n represents a number 0, 1 or 2, have now been found.

Furthermore, it has been found that the new substituted 1-arylpyrazoles of the general formula (I) are obtained by one of the processes described below:

a) Substituted 1-aryl-4-mercapto-pyrazoles of the formula (Ia)

in which
R$^1$, R$^2$, Ar and n have the abovementioned meaning and R$^{3-1}$ represents hydrogen or amino, are obtained when pyrazole derivatives of the formula (II)

in which
R$^1$, R$^{3-1}$ and Ar have the abovementioned meanings, are reacted with sulphenyl halides of the formula (III)

R$^2$—S—Hal (III)

in which
R$^2$ has the abovementioned meaning and Hal represents halogen, in particular chlorine or bromine, if appropriate in the presence of a diluent and if appropriate in the presence of a reaction auxiliary.

b) Substituted 1-arylpyrazoles of the formula (Ib)

in which
R$^1$, R$^2$, R$^{3-1}$ have the abovementioned meanings and n represents the number 1 or 2, are obtained when compounds of the formula (Ia)

in which
R$^1$, R$^2$ and R$^{3-1}$ have the abovementioned meanings, are oxidized using oxidants, if appropriate in the presence of a diluent and if appropriate in the presence of a catalyst.

Other preparation methods for the compounds of the formula (I) according to the invention are given hereinbelow by way of example, but not by limitation, R$^1$, R$^2$, R$^4$, R$^5$, R$^6$, R$^7$, Ar and n having the abovementioned meaning:

c) Reaction of substituted 1-arylpyrazoles of the formula (Ic) (R$^{3-1}$=NH$_2$) with acid halides of the formula (IV) (Hal=chlorine):

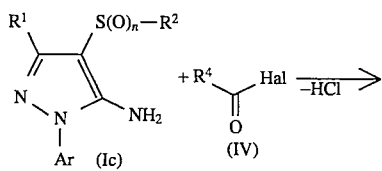
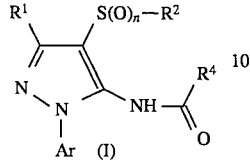

d) Reaction of substituted 1-arylpyrazoles of the formula (Ic) ($R^{3-1}=NH_2$) with acetals of the formula (V) ($R^8$=alkyl):

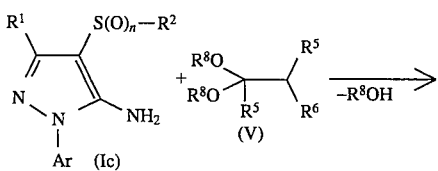
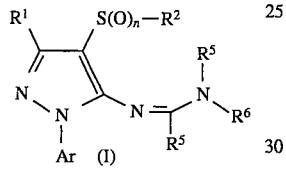

e) Reaction of substituted 1-arylpyrazoles of the formula (Ic) ($R^{3-1}=NH_2$) with tetrahydrofuran derivatives of the formula (VI) ($R^8$=alkyl):

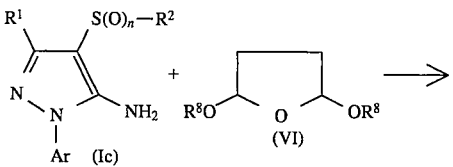
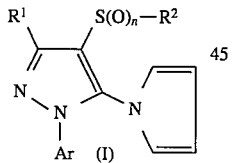

f) Reaction of substituted 1-arylpyrazoles of the formula (Ic) ($R^{3-1}=NH_2$) with aldehydes or ketones of the formula (VII):

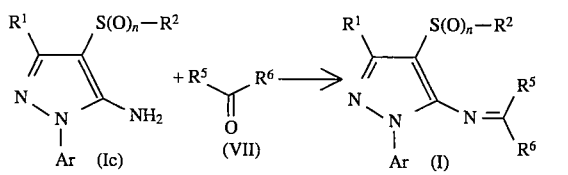

g) Reaction of substituted 1-arylpyrazoles of the formula (Ic) ($R^{3-1}=NH_2$) with ortho esters of the formula (VIII):

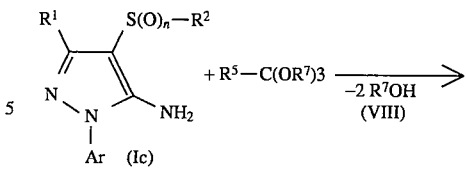

h) Reaction of substituted 1-arylpyrazoles of the formula (Ic) ($R^{3-1}=NH_2$) with tribromomethane, of the formula (IX):

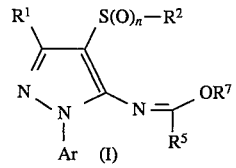
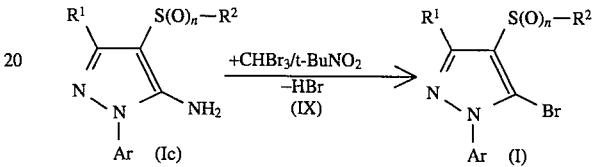

i) Reaction of Substituted 1-arylpyrazoles of the formula (Ic) ($R^{3-1}=NH_2$) with nucleophiles NU:

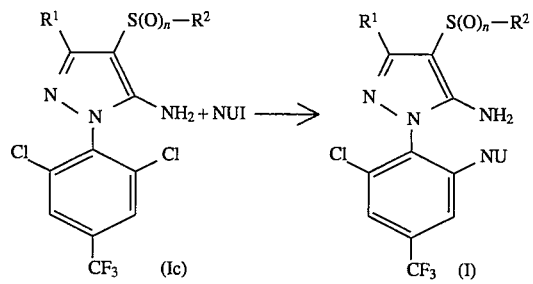

The invention preferably relates to compounds of the formula (I) in which $R^1$ represents hydrogen, cyano, ($C_1$-$C_6$)-alkyl, (C1-C4)-alkoxy-($C_1$-$C_4$)-alkyl, ($C_1$-$C_4$)-halogenoalkyl or ($C_1$-$C_2$)-cyanoalkyl, $R^2$ represents difluoroethyl or trifluoroethyl, $R^3$ represents hydrogen, amino, halogen or one of the following groups

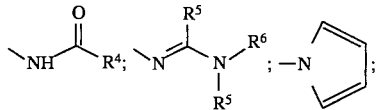

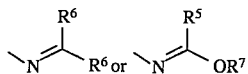

in which $R^4$ represents ($C_1$-$C_6$)-alkyl, ($C_1$-$C_6$)-halogenoalkyl having 1–3 halogen atoms, ($C_1$-$C_6$)-alkoxy-($C_1$-$C_6$)-alkyl, or phenyl which is optionally monosubstituted to trisubstituted by identical or different substituents, $R^5$ represents hydrogen or ($C_1$-$C_6$)-alkyl, $R^6$ represents hydrogen, $(C_1-C_6)$-alkyl, or phenyl which is optionally monosubstituted to trisubstituted by identical or different substituents, $R^7$ represents $(C_1-C_6)$-alkyl or $R^5$ and $R^6$ together with the carbon atom to which they are bonded represent optionally substituted pyridyl, Ar represents phenyl or pyridyl, each of which is optionally monosubstituted to trisubstituted by identical or different substituents from the series comprising halogen, halogeno $(C_1-C_6)$alkyl, halogeno$(C_1-C_6)$alkylthio, halogeno$(C_1-C_6)$alkoxy, alkoxy, hydrazino, $(C_1-C_6)$-dialkylhydrazino, amino, amino$(C_1-C_6)$alkyl, diamino$(C_1-C_6)$alkyl, imino$(C_1-C_6)$-alkyl, cyano, $(C_1-C_6)$alkylthio or the group

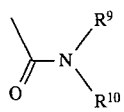

in which $R^9$ and $R^{10}$ are identical or different and represent hydrogen or $(C_1-C_6)$-alkyl, and n represents a number 0, 1 or 2.

In particular, the invention relates to compounds of the formula (I) in which $R^1$ represents hydrogen, cyano, $(C_1-C_4)$-alkyl, $(C_1-C_4)$-alkoxy-$(C_1-C_2)$-alkyl, $(C_1-C_2)$-halogenoalkyl having 1 to 5 identical or different fluorine, chlorine or bromine atoms, or cyanomethyl, $R^2$ represents difluoroethyl or trifluoroethyl, $R^3$ represents hydrogen, amino, bromine or one of the following groups

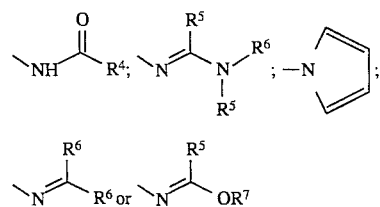

in which $R^4$ represents $(C_1-C_4)$-alkyl, $(C_1-C_4)$-halogenoalkyl having 1–3 halogen atoms, $(C_1-C_4)$-alkoxy-$(C_1-C_2)$-alkyl, or phenyl which is optionally monosubstituted to trisubstituted by identical or different substituents, $R^5$ represents hydrogen or $(C_1-C_4)$-alkyl, $R^6$ represents hydrogen, $(C_1-C_4)$-alkyl, phenyl which is optionally monosubstituted or disubstituted by identical or different substituents, or 4-hydroxy-3-methoxyphenyl, $R^7$ represents $(C_1-C_4)$-alkyl or $R^5$ and $R^6$ together with the carbon atom to which they are bonded represent optionally substituted pyridyl, Ar represents phenyl or pyridyl, each of which is optionally monosubstituted to trisubstituted by identical or different substituents from the series comprising fluorine, chlorine, trifluoromethyl, trifluoromethylthio, trifluoromethoxy, methoxy, hydrazino, dimethylhydrazino, amino, methylamino, dimethylamino, iminomethyl, cyano, methylthio or the group

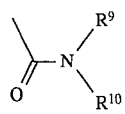

in which $R^9$ and $R^{10}$ are identical or different and represent hydrogen or $(C_1-C_4)$-alkyl, and n represents a number 0, 1 or 2.

Very particularly preferred compounds of the formula (I) are those in which $R^1$ represents hydrogen, cyano, $(C_1-C_4)$-alkyl, methoxymethyl, ethoxymethyl, methoxyethyl, ethoxyethyl, trifluoromethyl, bromomethyl or cyanomethyl, $R^2$ represents 1,1-difluoroethyl or 2,2,2-trifluoroethyl, Ar represents phenyl which is disubstituted or trisubstituted by identical or different substituents, substituents in the 2-position being fluorine or chlorine, in the 4-position trifluoromethyl and in the 6-position fluorine, chlorine, cyano, methoxy, methylthio, trifluoromethyl, trifluoromethoxy or trifluoromethylthio, or Ar represents a 2-pyridyl radical which is substituted in the 4-position by trifluoromethyl and in the 6-position by fluorine or chlorine, and $R^3$ and n have the abovementioned meanings.

The abovementioned general definitions or those where preferred ranges have been mentioned apply to the end products of the formula (I) and, analogously, to the starting materials or intermediates required in each case for the preparation. The definitions can be combined with each other, that is to say any desired combinations between the preferred ranges indicated are possible.

The hydrocarbon radicals mentioned in the definition of the radicals, such as alkyl, alkoxy, alkoxyalkyl and alkylthio, are straight-chain or branched, even if this is not stated expressly.

Halogen generally represents fluorine, chlorine, bromine or iodine, preferably fluorine, chlorine or bromine, in particular fluorine or chlorine.

The following substituted 1-arylpyrazoles of the general formula (I) may be mentioned individually in addition to the compounds mentioned in the Preparation Examples:

TABLE 1

| | $R^1$ | $S(O)_n$—$R^2$ | | (I) |
| | | | $R^3$ | |
| | $N\diagdown N$ | | | |
| | Ar | | | |

| $R^1$ | $R^2$ | $R^3$ | n | Ar |
|---|---|---|---|---|
| H | CF$_2$CH$_3$ | NH$_2$ | 0 | 2-Cl, 4-CF$_3$-pyridyl |

TABLE 1-continued

Structure (I): pyrazole with R¹ at 3-position, S(O)ₙ—R² at 4-position, R³ at 5-position, N1 substituted with Ar.

| R¹ | R² | R³ | n | Ar |
|---|---|---|---|---|
| CH₂Br | CF₂CH₃ | NH₂ | 0 | 2,6-dichloro-4-(trifluoromethyl)phenyl |
| CH₂Br | CF₂CH₃ | NH₂ | 0 | 3-chloro-5-(trifluoromethyl)-2-pyridyl |
| CH₃OCH₂ | CF₂CH₃ | NH₂ | 1 | 2,6-dichloro-4-(trifluoromethyl)phenyl |
| CH₃OCH₂ | CF₂CH₃ | NH₂ | 2 | 2,6-dichloro-4-(trifluoromethyl)phenyl |
| CH₃OCH₂ | CF₂CH₃ | NH₂ | 1 | 3-chloro-5-(trifluoromethyl)-2-pyridyl |
| CH₃OCH₂ | CF₂CH₃ | NH₂ | 2 | 3-chloro-5-(trifluoromethyl)-2-pyridyl |
| CH₃OCH₂ | CH₂CF₃ | NH₂ | 2 | 2,6-dichloro-4-(trifluoromethyl)phenyl |
| CH₃OCH₂ | CH₂CF₃ | NH₂ | 1 | 3-chloro-5-(trifluoromethyl)-2-pyridyl |
| CN | CF₂CH₃ | NH₂ | 1 | 2,6-dichloro-4-(trifluoromethyl)phenyl |
| CN | CH₂CF₃ | NH₂ | 1 | 2,6-dichloro-4-(trifluoromethyl)phenyl |
| H | CF₂CH₃ | NH₂ | 1 | 2,6-dichloro-4-(trifluoromethyl)phenyl |
| H | CF₂CH₃ | NH₂ | 2 | 2,6-dichloro-4-(trifluoromethyl)phenyl |
| H | CF₂CH₃ | NH₂ | 1 | 3-chloro-5-(trifluoromethyl)-2-pyridyl |
| H | CF₂CH₃ | NH₂ | 2 | 3-chloro-5-(trifluoromethyl)-2-pyridyl |
| H | CF₂CH₃ | NH₂ | 2 | 2,6-dichloro-4-(trifluoromethyl)phenyl |
| H | CH₂CF₃ | NH₂ | 1 | 3-chloro-5-(trifluoromethyl)-2-pyridyl |

TABLE 1-continued $$R^1 \quad S(O)_n-R^2 \quad (I)$$

(pyrazole structure with $R^1$, $R^3$, $S(O)_n$-$R^2$, and Ar substituents)

| R¹ | R² | R³ | n | Ar |
|---|---|---|---|---|
| H | CH₂CF₃ | NH₂ | 2 | 3-chloro-5-(trifluoromethyl)-2-pyridyl |
| CH₃ | CF₂CH₃ | NH₂ | 2 | 2,6-dichloro-4-(trifluoromethyl)phenyl |
| CH₃ | CF₂CH₃ | NH₂ | 1 | 3-chloro-5-(trifluoromethyl)-2-pyridyl |
| CH₃ | CH₂CF₃ | NH₂ | 1 | 3-chloro-5-(trifluoromethyl)-2-pyridyl |

If, for example, 5-amino-1-(2,6-dichloro-4-trifluoromethylphenyl)-3-methyl-pyrazole and 1,1-difluoroethylsulphenyl chloride are used as starting substances, the course of the reaction of process (a) according to the invention can be represented by the following equation:

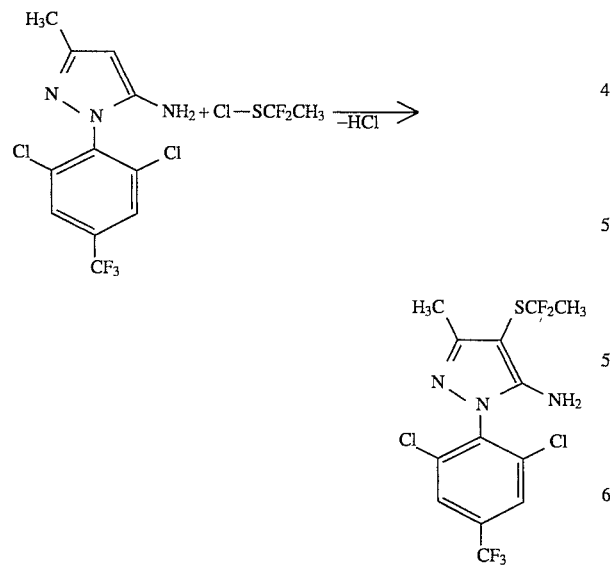

If, for example, 5-amino-3-methoxymethyl-4-(2,2,2-trifluoromethylthio)-1-[(3-chloro-5-trifluoromethyl)-2-pyridyl]-pyrazole is used as starting substance, H₂O₂ as oxidant and sodium tungstate as catalyst, the course of the reaction of process (b) according to the invention can be represented by the following equation:

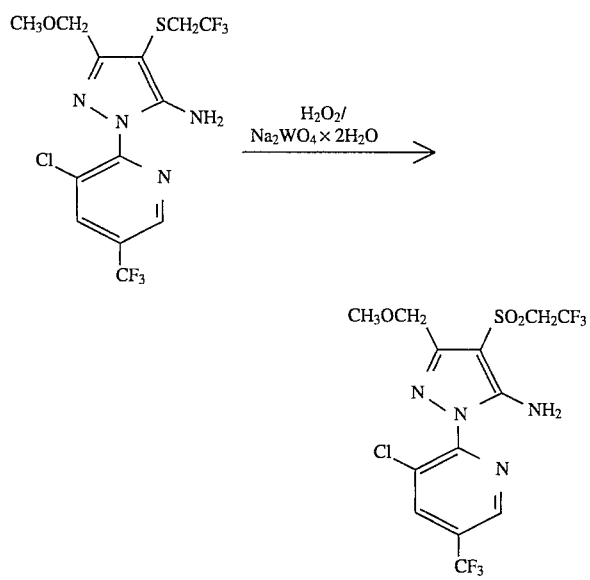

If, for example, 5-amino-4-(1,1-difluoroethylthio)-1-(2,6-dichloro-4-trifluoromethyl-phenyl)-3-methoxymethylpyrazole and methoxyacetyl chloride are used as starting substances, the course of the reaction of process (c) according to the invention can be represented by the following equation:

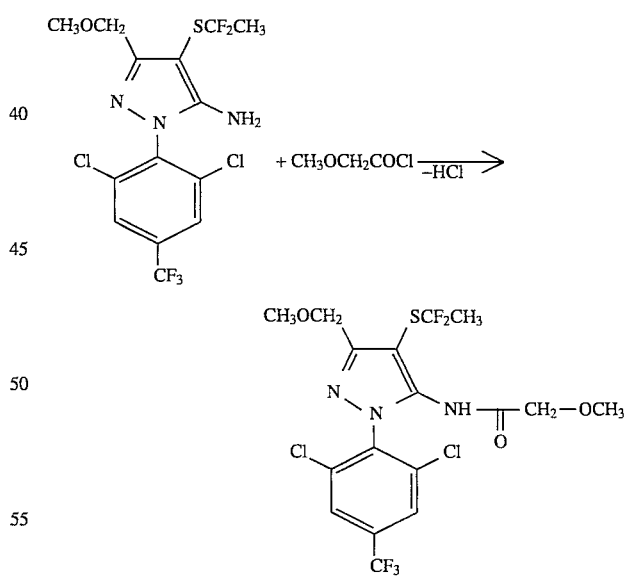

If, for example, 5-amino-3-cyano-4-(1,1-difluoroethylthio)-1-thio)-1-(2,6-dichloro-4-trifluoromethylphenyl)-pyrazole and dimethylformamide dimethyl acetal are used as starting substances, the course of the reaction of process (d) according to the invention can be represented by the following equation:

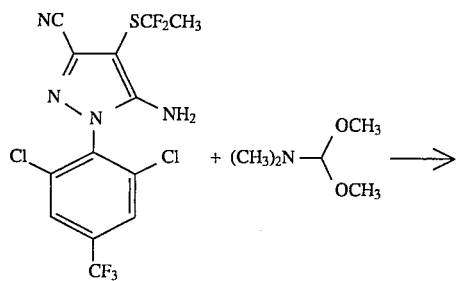

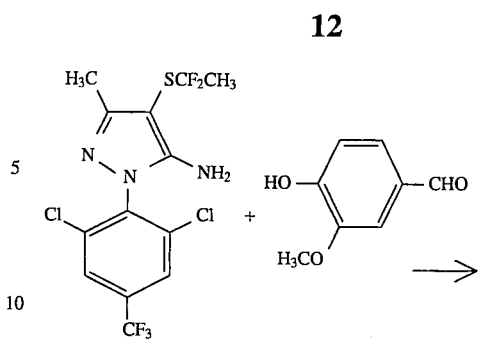

If, for example, 5-amino-4-(1,1-difluoroethylthio)-1-(2,6-dichloro-4-trifluoromethyl-phenyl)-pyrazole and 2,5-dimethoxytetrahydrofuran are used as starting substances, the course of the reaction of process (e) according to the invention can be represented by the following equation:

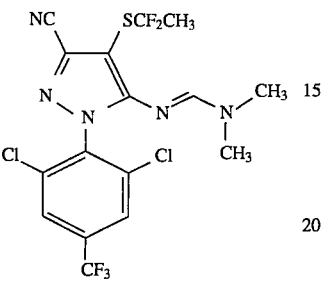

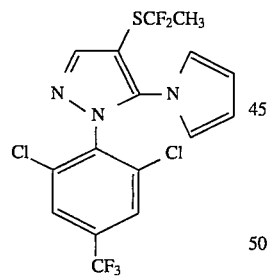

If, for example, 5-amino-1-(2,6-dichloro-4-trifluoromethylphenyl)-3-methyl-4-(1,1-difluoroethylthio)-pyrazole and 3-methoxy-4-hydroxybenzaldehyde are used as starting substances, the course of the reaction of process (f) according to the invention can be represented by the following equation:

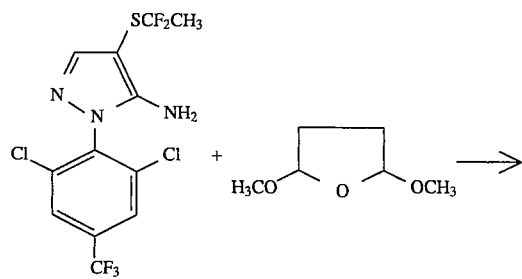

If, for example, 5-amino-1-(2,6-dichloro-4-trifluoromethylphenyl)-3-methyl-4-(1,1-difluoroethylthio)-pyrazole and ethyl orthoformate are used as starting substances, the course of the reaction of process (g) according to the invention can be represented by the following equation:

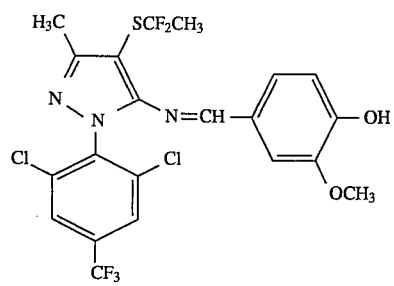

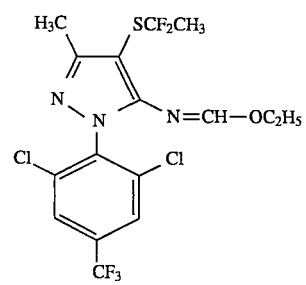

If, for example, 5-amino-4-(1,1-difluoroethylthio)-1-(2,6-dichloro-4-trifluoromethylphenyl)-pyrazole, tribromomethane and tert-butyl nitrite are used as starting substances, the course of the reaction of process (h) according to the invention can be represented by the following equation:

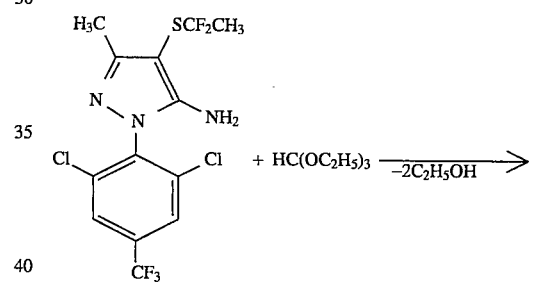

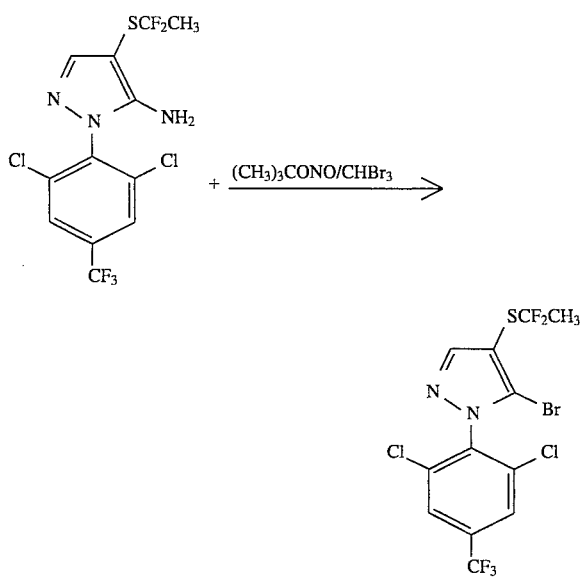

If, for example, 5-amino-4-(1,1-difluoroethylthio)-1-(2,6-dichloro-4-trifluoromethylphenyl)-pyrazole and hydrazine hydrate are used as starting substances, the course of the reaction of process (i) according to the invention can be represented by the following equation:

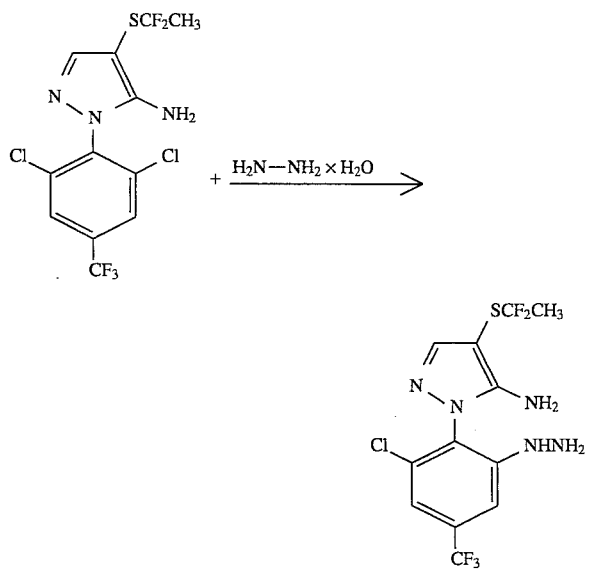

Some of the pyrazole derivatives of the formula (II) to be used as starting substances for carrying out process (a) according to the invention are known, or they can be obtained by known processes (cf. for example EP-A 295 117, EP-A 154 115, EP-A 201 852).

The pyrazole derivatives of the formula (IIa)

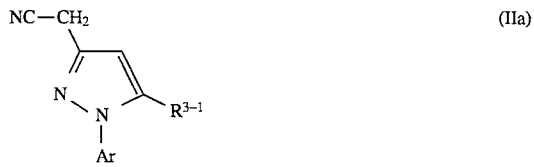

in which $R^{3-1}$ and Ar have the abovementioned meaning, are new and a subject of the invention.

The compounds of the formula (IIa) can be obtained by generally customary and known processes by heating bromomethyl-pyrazoles of the formula (IIb)

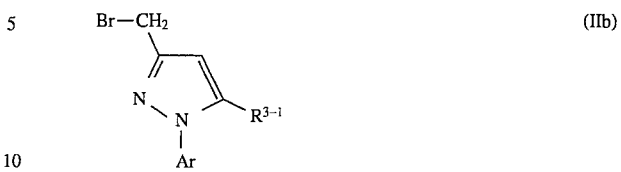

in which $R^{3-1}$ and Ar have the abovementioned meaning, together with alkali metal cyanides, such as, for example, sodium cyanide or potassium cyanide, if appropriate in the presence of an inert diluent, such as, for example, water, and in the presence of a phase transfer catalyst, such as, for example, TEBA, at temperatures between 40° C. and 100° C., preferably 70° C. to 100° C. (cf. Preparation Example).

If, for example, 5-amino-1-(2,6-dichloro-4-trifluoromethylphenyl)-3-bromomethyl-pyrazole is used as starting substance and an aqueous sodium cyanide solution and TEBA as phase transfer catalyst, the course of the reaction of the process according to the invention can be represented by the following equation:

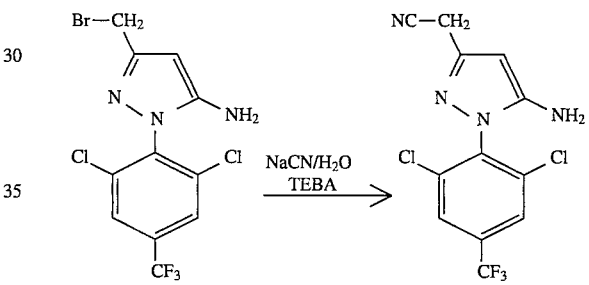

The bromomethylpyrazoles of the formula (IIb), which are required as starting compounds for the preparation of the pyrazole derivatives of the formula (IIa), are new and a subject of the invention.

Compounds of the formula (IIb) are obtained by generally customary and known processes by heating methoxymethylpyrazoles of the formula (IIc):

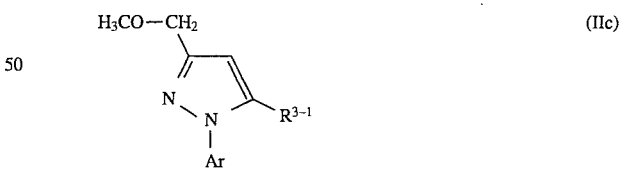

in which $R^{3-1}$ and Ar have the abovementioned meaning, together with a 48% strength solution of hydrogen bromide in glacial acetic acid at temperatures between 60° C. and 130° C., preferably at temperatures between 90° C. and 130° C. (cf. Preparation Examples).

If, for example, 5-amino-1-(2,6-dichloro-4-trifluoromethylphenyl)-3-methoxypyrazole and 48% strength solution of hydrogen bromide in glacial acetic acid are used as starting substances, the course of the reaction of the process according to the invention can be represented by the following equation:

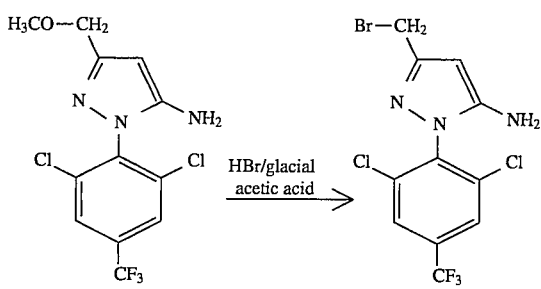

The methoxymethylpyrazoles of the formula (IIc), which are required as starting compounds for the preparation of the bromomethylpyrazole derivatives of the formula (IIb), are new and also a subject of the invention.

The compounds of the formula (IIc) can be obtained by heating arylhydrazines of the formula (X)

Ar—NHNH₂ (X)

in which

Ar has the abovementioned meaning, together with 2-amino-1-cyano-3-methoxy-propene of the formula (XI)

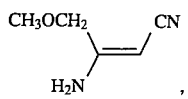
(XI)

if appropriate in the presence of an inert organic solvent, such as, for example, alcohols, preferably methanol or ethanol, or acetic acid, or mixtures of methanol and acetic acid or ethanol and acetic acid, at temperatures between 50° C. and 130° C., preferably 60° C. and 120° C. To carry out the process, 1 to 4 mol, preferably 1 to 2 mol, of 1-cyano-2-amino-3-methoxy-propene of the formula (XI) is generally employed per mole of arylhydrazine of the formula (X). The reaction is carried out and the compounds of the formula (IVc) are worked up and isolated in the customary manner.

If, for example, 2,6-dichloro-4-trifluoromethylphenylhydrazine and 1-cyano-2-amino-3-methoxy-propene are used as starting substances, the course of the reaction of the process according to the invention can be represented by the following equation:

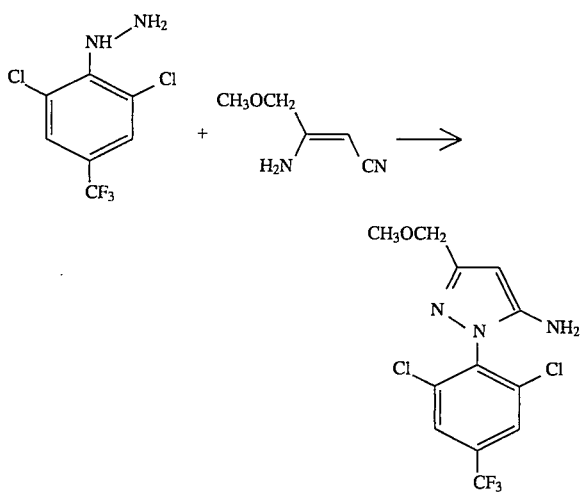

The arylhydrazines of the formula (X), which are required as starting substances, are generally known compounds of organic chemistry.

2-Amino-1-cyano-3-methoxypropene, of the formula (XI), which is furthermore required for the preparation of the methoxymethylpyrazoles of the formula (IIc), is new and a subject of the invention.

2-Amino-1-cyano-3-methoxy-propene, of the formula (XI), is obtained when methoxyacetonitrile, of the formula (XII),

$CH_3OCH_2$—CN (XII)

is heated together with acetonitrile and, if appropriate, in the presence of an inert organic solvent, such as, for example, ethers, preferably diethyl ether, dibutyl ether, glycol dimethyl ether and diglycol methyl ether, tetrahydrofuran and dioxane, or in mixtures of acetonitrile and these solvents and in the presence of bases, such as, for example, sodium hydride or potassium tert-butylate, at temperatures between 20° C. and 150° C., preferably 20° C. and 100 ° C. To carry out the process, methoxyacetonitrile, the base in question and acetonitrile are generally employed in approximately-equimolar amounts. However, it is also possible to use one of the two components employed in each case in a larger excess. The reaction is carried out and the compounds of the formula (XI) are worked up and isolated in the customary manner (cf. Preparation Examples).

The compound of the formula (XI) can exist in the form of geometric isomers (E/Z isomers) or of variously composed mixtures of isomers. The invention claims the use of the pure isomers as well as of the isomer mixtures. For simplicity's sake, the text hereinbelow will always mention compounds of the formula (XI), even though this is to be understood as meaning the pure compounds and also their mixtures which contain various amounts of E/Z isomers.

Formula (III) provides a general definition of the sulphenyl halides furthermore required as starting substances for carrying out the process (a) according to the invention. In this formula (III), $R^2$ preferably represents those radicals which have already been mentioned in connection with the description of the substances of the formula (I) according to the invention as being preferred for this substituent.

The sulphenyl halides of the formula (III) are generally known compounds of organic chemistry.

Formula (Ia) provides a general definition of the 1-aryl-4-mercapto-pyrazoles required as starting substances for carrying out the process (b) according to the invention. In this formula (Ia), $R^1$, $R^2$, $R^{3-1}$ and Ar preferably represent those radicals and indices which have already been mentioned in connection with the description of the substances of the formula (I) according to the invention as being preferred for these substituents.

The compounds of the formula (Ia) are compounds according to the invention and can be obtained by process (a).

Formula (Ic) provides a general definition of the 1-aryl-4-pyrazoles required as Starting substances for carrying out the processes (c), (d), (e), (f), (g), (h) and (i) according to the invention. In this formula (Ic), $R^1$, $R^2$, Ar and n preferably represent those radicals and indices which have already been mentioned in connection with the description of the substances of the formula (I) according to the invention as being preferred for these substituents.

The compounds of the formula (Ic) are compounds according to the invention and can be obtained by processes (a) or (b).

The compounds of the formulae (IV), (V), (VI), (VII), (VIII) and (IX), which are furthermore required as starting compounds, are generally known compounds of organic chemistry.

Suitable nucleophiles (NuI) for carrying out the process (i) according to the invention are all customary reagents of organic chemistry which are suitable for such reactions. Examples which may be mentioned, but not by limitation, are: alcoholates, hydrazine derivatives and cyanides.

Suitable diluents for carrying out the process (a) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride; ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile; amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, or acids, such as, for example, acetic acid.

If appropriate, process (a) according to the invention can be carried out in the presence of a reaction auxiliary. Suitable reaction auxiliaries are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out the process (a) according to the invention, the reaction temperatures can be varied within a substantial range. In general, the process is carried out at temperatures between −20° C. and +120° C., preferably at temperatures between 0° C. and +50° C.

For carrying out the process (a) according to the invention, 1.0 to 2.5 mol, preferably 1.0 to 1.5 mol, of sulphenyl halide of the formula (III) and, if appropriate, 1.0 to 2.5 mol, preferably 1.0 to 1.5 mol, of reaction auxiliary are generally employed per mole of pyrazole derivatives of the formula (II). The reaction is carried out and the reaction products of the formula (Ia) are worked up and isolated by generally customary processes.

Suitable oxidants for carrying out the process (b) according to the invention are all customary oxidants which can be used for the oxidation of sulphur. Particularly suitable are hydrogen peroxide, organic peracids, such as, for example, peracetic acid, m-chloroperbenzoic acid, p-nitroperbenzoic acid or atmospheric oxygen.

Diluents which are suitable for carrying out the process (b) according to the invention are also inert organic solvents. The following are preferably used: hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethylformamide.

If appropriate, process (b) according to the invention can be carried out in the presence of an acid-binding agent. All organic and inorganic acid-binding agents which can conventionally be used are suitable. The following are preferably used: alkaline earth metal hydroxides, alkaline earth metal acetates, alkaline earth metal carbonates, alkali metal hydroxides, alkali metal acetates or alkali metal carbonates, such as, for example, calcium hydroxide, sodium hydroxide, sodium acetate or sodium carbonate.

If appropriate, process (b) according to the invention can be carried out in the presence of a suitable catalyst. All metal salt catalysts which are generally customary for such sulphur oxidations are suitable. Ammonium molybdate and sodium tungstate may be mentioned in this context by way of example.

When carrying out the process (b) according to the invention, the reaction temperatures can be varied within a substantial range. In general, the process is carried out at temperatures between −20° C. and +70° C., preferably at temperatures between 0° C. and +50° C.

To carry out process (b) according to the invention, 0.8 to 1.2 mol, preferably equimolar amounts, of oxidant are generally employed per mole of substituted 1-arylpyrazole of the formula (Ia), if it is intended to interrupt the oxidation of the sulphur at the sulphoxide level. 1.8 to 3.0 mol, preferably twice the molar amounts, of oxidant are generally employed per mole of substituted 1-arylpyrazole of the formula (Ia) to oxidize the sulphoxide to the sulphone. The reaction is carried out and the end products of the formula (Ib) are worked up and isolated by customary processes.

The active compounds are well tolerated by plants, have a favourable toxicity to warm-blooded species and are suitable for combating animal pests, in particular insects, arachnids and nematodes, which occur in agriculture, in forests, in the protection of stored products and of materials, and in the hygiene sector. They can preferably be used as plant protection agents. They are active against normally sensitive and resistant species and against all or individual development stages. They abovementioned pests include:

From the order of the Isopoda, for example, *Oniscus asellus, Armadillidium vulgate* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanlea, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example, *Reticulitermes spp.*

From the order of the Anopolura, for example, *Phylloxera vastatrix, Pemphigus spp., Pediculus humanus corporis, Haematopinus spp.* and *Linognathus spp., Bovicola spp.*

From the order of the Mallophaga, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piestoa quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hya-*

*lopterus arundinis, Macrosiphum avenae, Myzus spp., Photodon humuli, Rhopalosiphum padi, Empoasca spp., Euscelis bilobatus, Nephotettix cincticeps, Lecanium corni, Saissetia oleae, naodelphax striatellus, Nilaparvata lugens, Aonidiella aurantii, Aspidiotus hederae, Psuedococcus spp.* and *Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.*

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp., Ctenocephalides spp.*

From the order of the Arachnida, for example, *Scorpio maurus* and *Latrodectus mactans.*

From the order of the Acarina, for example, *Acarus siro, Argas. spp., Ornithodoros spp., Dermanyssus gallinae, Eriophyes ribis, Phyllocoptruta oleivora, Boophilus spp., Rhipicephalus spp., Amhlyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The plant-parasitic nematodes include *Pratylenchus spp., Radopholus similis, Ditylenchus dipsaci, Tylenchulus semipenetrans, Heterodera spp., Meloidogyne spp., Aphelenchoides spp., Longidorus spp., Xiphinema spp.* and *Trichodorus spp.*

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from the formulations, as a mixture with other active compounds, such as insecticides, attractants, sterilizing agents, acaricides, nematicides, fungitides, growth-regulating substances or herbicides. The insecticides include, for example, phosphates, carbamates, carboxylates, chlorinated hydrocarbons, phenylureas and substances produced by microorganisms.

The following compounds may be mentioned:

acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mevinphos, mesulfenphos, methacrifos, methamidophos, naled, omethoate, oxydemeton M, oxydeprofos, parathion A, parathion M, phenthoate, phorate, phosalone, phosmet, phosphamdon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazine, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyridinyl)methyl]-N'-cyano-N-methylethane-imide-amide (NI-25), abamectin, amitrazine, avermectin, azadirachtin, bensultap, *Bacillus thuringiensis*, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimiphos, tefluthrin, terbufos, thiodicarb, thiafenox, azocyclotin, butylpyridaben, clofentezine, cyhexatin, diafenthiuron, diethion, emaanectin, fenazaquin, fenbutatin oxide, fenothiocarb, fenpropathrin, fenypyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and 4-bromo-2-(4-chlorophenyl)-1-(ethoxymethyl)-5-(trifluoromethyl)-1H-pyrrole-3-carbonitrile (AC 303630).

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent-residual action on wood and clay as well as a good stability to alkali.

The preparation of the compounds of the formula (I) according to the invention will be illustrated with the aid of the following Examples:

Unless otherwise indicated, percentages are by weight.

PREPARATION EXAMPLES

Example 1

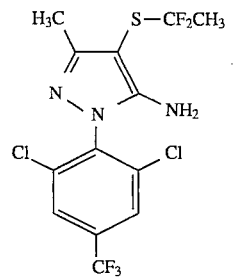

(Process Variant a)

15.5 g (0.05 mol) of 5-amino-1-(2,6-dichloro-4-trifluoromethylphenyl)-3-methyl-pyrazole are dissolved in 120 ml of absolute dichloromethane, and 4.35 g (0.055 mol) of absolute pyridine are added. The mixture is then cooled to 0°–5° C., and 7.3 g (0.055 mol) of 1,1-difluoroethylsulphenyl chloride are added dropwise. The mixture is stirred for 3 hours at 0° C. and then overnight at room temperature. The mixture is subsequently washed twice with water and dried using magnesium sulphate, and the solvent is stripped off in vacuo.

13.1 g (65% of theory) of 5-amino-3-methyl-4-(1,1-difluoroethylthio)-1-(2,6-dichloro-4-trifluoromethylphenyl)-pyrazole of melting point 123°–125° C. are obtained.

Example 2

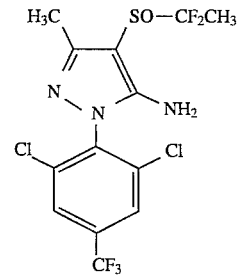

(Process Variant b)

4.6 g (0.0113 mol) of 5-amino-3-methyl-4-(1,1-difluoroethylthio)-1-(2,6-dichloro-4-trifluoromethylphenyl)-pyrazole are introduced into 30 ml of 80% strength sulphuric acid in the course of approximately 10 minutes at 25° C.–35° C. 1 ml of 35% strength $H_2O_2$ solution is added dropwise with cooling, and stirring is subsequently continued for 20 hours at room temperature. The reaction mixture is then diluted with water, and the precipitate is filtered off with suction. After stirring with petroleum ether, 1.8 g (38% of theory) of 5-amino-3-methyl-4-(1,1-difluoroethylsulphinyl)-1-(2,6-dichloro-4-trifluoromethylphenyl)-pyrazole of melting point 177°–179° C. are obtained.

Example 3

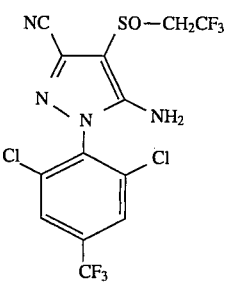

(Process Variant b)

2 g (0.005 mol) of 5-amino-3-cyano-4-(2,2,2-trifluoroethylthio)-1-(2,6-dichloro-4-trifluoromethylphenyl)-pyrazole are dissolved in 10 ml of acetic acid, and a spatula-tip full of sodium tungstate is added. 6 g (0.052 mol) of 30% strength $H_2O_2$ solution are added dropwise to this solution at room temperature. Stirring is continued for 18 hours. Since a thin-layer chromatogram revealed that the reaction was still incomplete, a further 6 g (0.052 mol) of 30% strength $H_2O_2$ solution are added, and the mixture is stirred for a further 18 hours at room temperature. The reaction mixture is then diluted with approximately 100 ml of water and extracted using dichloromethane. The dichloromethane phase is dried over magnesium sulphate and evaporated in vacuo using a rotary evaporator.

1 g (47% of theory) of 5-amino-3-cyano-4-(2,2,2-trifluoroethylsulphonyl)-1-(2,6-dichloro-4-trifluoromethylphenyl)-pyrazole of melting point 157° C. is obtained.

The following end products of the formula (I)

can be obtained analogously to Preparation Examples 1, 2 and 3 and in accordance with the abovementioned process (a) or (b):

TABLE 2

| Ex. No. | $R^1$ | $R^2$ | $R^3$ | n | Ar | Physical constants |
|---|---|---|---|---|---|---|
| 4 | —$CH_2OCH_3$ | —$CF_2CH_3$ | $NH_2$ | 0 | 2,6-Cl, 4-$CF_3$-phenyl | $^1H$—NMR δ*)=(8.2(s, 2H); 6.2(s, $NH_2$); 4.3(s, 2H); 3.25(s, 3H); 1.88(t, 3H)) |
| 5 | CN | —$CF_2CH_3$ | $NH_2$ | 0 | 2,6-Cl, 4-$CF_3$-phenyl | m.p.: 166° C. |
| 6 | H | —$CF_2CH_3$ | $NH_2$ | 0 | 2,6-Cl, 4-$CF_3$-phenyl | m.p.: 68–69° C. |
| 7 | —$CH_2OCH_3$ | —$CF_2CH_3$ | $NH_2$ | 0 | 2-Cl, 4-$CF_3$-pyridyl | $^1H$—NMR δ**)=(8.99(d, 1H); 8.78 (d, 1H); 6.3(bs, $NH_2$); 4.3(s, 2H); 3.21(s, 3H); 1.90(t, 3H)) |
| 8 | $CH_3$ | —$CF_2CH_3$ | $NH_2$ | 0 | 2-Cl, 4-$CF_3$-pyridyl | $^1H$—NMR δ*)=(8.6(d, 1H); 8.15 (d, 1H); 5.5(bs, $NH_2$); 2.3(s, 3H); 1.9(t, 3H)) |
| 9 | $CH_3$ | —$CF_3CH_3$ | $NH_2$ | 2 | 2,6-Cl, 4-$CF_3$-phenyl | $^1H$—NMR δ**)=(9.05(d, 1H); 8.82 (d, 1H); 6.89(bs, $NH_2$); 2.20 (s, 3H); 2.02(t, 3H)) |

TABLE 2-continued
| Ex. No. | R¹ | R² | R³ | n | Ar | Physical constants |
|---|---|---|---|---|---|---|
| 10 | CH₃ | —CF₂CH₃ | NH₂ | 2 | 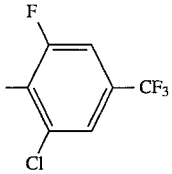 | ¹H—NMR δ*)=(7.68(bs); 7.49(d); 4.28(bs, NH₂); 2.3(s, CH₃); 1.9 (t, 3H)) |
| 11 | —CH₂OCH₃ | —CF₂CH₃ | NH₂ | 0 | 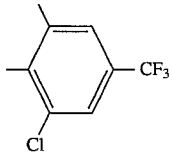 | ¹H—NMR δ**=)=(8.05(m, 2H); 6.25 (bs, NH₂); 4.3(m, 2H); 3.22(s, 3H); 1.89(t, 3H)) |
| 12 | CH₃ | —CF₂CH₃ | NH₂ | 0 | 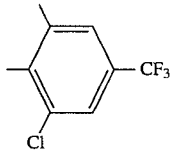 | ¹H—NMR δ**)=(8.03(m, 2H); 6.15 (bs, NH₂); 2.1(s, 3H); 1.85(t, 3H)) |
| 13 | —CH₂OCH₃ | —CH₂CF₃ | NH₂ | 0 | 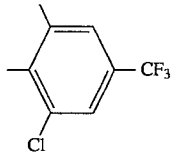 | m.p.: 77° C. |
| 14 | —CN | —CH₂CF₃ | NH₂ | 0 | 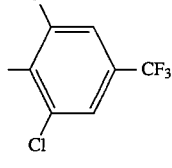 | ¹H—NMR δ**)=(7.8(s, 2H); 6.12 (bs, NH₂); 3.4(q, 2H)) |
| 15 | —CH₃ | —CH₂CF₃ | NH₂ | 0 | 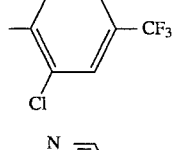 | m.p.: 126–128° C. |
| 16 | —CH₂OCH₃ | —CH₂CF₃ | NH₂ | 0 | 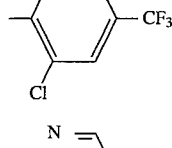 | ¹H—NMR δ**)=(8.95(d, 1H); 8.75 (d, 1H); 6.12(bs, NH₂); 4.32(s, 2H); 3.45(q, 2H); 3.28(s, 3H)) |
| 17 | —CH₃ | —CH₂CF₃ | NH₂ | 0 | 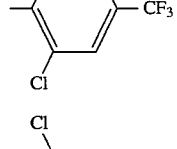 | m.p.: 36° C. |
| 18 | H | —CH₂CF₃ | NH₂ | 0 | 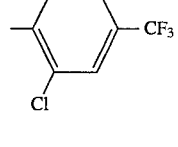 | m.p.: 90–92° C. |

TABLE 2-continued

| Ex. No. | R¹ | R² | R³ | n | Ar | Physical constants |
|---|---|---|---|---|---|---|
| 19 | —CH₂OCH₃ | —CH₂CF₃ | NH₂ | 1 | 2,6-Cl₂-4-CF₃-C₆H₂— | wax |
| 20 | H | —CH₂CF₃ | NH₂ | 1 | 2,6-Cl₂-4-CF₃-C₆H₂— | m.p.: 134–136° C. |
| 21 | CH₃ | —CH₂CF₃ | NH₁ | 1 | 2,6-Cl₂-4-CF₃-C₆H₂— | m.p.: 104–105° C. |
| 22 | —CN | —CF₂CH₃ | NH₂ | 2 | 2,6-Cl₂-4-CF₃-C₆H₂— | m.p.: 163° C. |
| 23 | —CH₂OCH₃ | —CH₂CF₃ | NH₂ | 2 | 3-Cl-5-CF₃-pyridin-2-yl | ¹H—NMR δ**)=(9.04(d, 1H); 8.85 (d, 1H); 6.71(bs, NH₂); 4.61(q, 2H); 4.40(s, 2H); 3.30(s, 3H)) |
| 24 | —CH₂OCH₃ | —CH₂CF₃ | NH₂ | 2 | 3-Cl-5-CF₃-pyridin-2-yl | |
| 25 | CH₃ | —CH₂CF₃ | NH₂ | 2 | 2,6-Cl₂-4-CF₃-C₆H₂— | m.p.: 160° C. |
| 26 | CH₂Br | —CF₂CH₃ | NH₂ | 0 | 2,6-Cl₂-4-CF₃-C₆H₂— | m.p.: 160° C. |

TABLE 2-continued

| Ex. No. | R¹ | R² | R³ | n | Ar | Physical constants |
|---|---|---|---|---|---|---|
| 27 | —C(CH₃)₃ | —CF₂CH₃ | NH₂ | 0 | 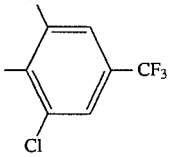 | m.p.: 117° C. |

Example 28

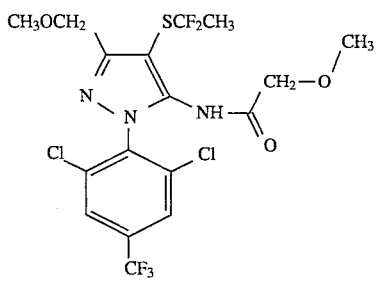

(Process Variant c)

2 g (0.005 mol) of 5-amino-4-(1,1-difluoroethylthio)-1-(2,6-dichloro-4-trifluoromethylphenyl)-3-methoxymethylpyrazole are dissolved in 20 ml of anhydrous toluene, and 2 g (0.025 mol) of anhydrous pyridine are added. 0.8 g (0.007 mol) of methoxyacetyl chloride are added dropwise in the course of 5 minutes, and stirring is subsequently continued for 12 hours at 80° C. For working-up, the mixture is diluted with water, and the organic phase is separated off and dried over magnesium sulphate and concentrated in vacuo. 1.4 g (60% of theory) of 5-methoxymethyl-carbonylamino)-4-(1,1-difluoroethylthio)-1-(2,6-dichloro-4-trifluoromethyl-phenyl)-3-methoxymethylpyrazole remain as a brown wax.

¹H-NMR δ*)=(10.3 ppm (1H); 8.2 ppm (2H); 4.48 ppm (2H); 3.9 ppm (2H); 3.29 ppm (3H); 3.18 ppm (3H); 1.89 ppm (3H)).

Example 29

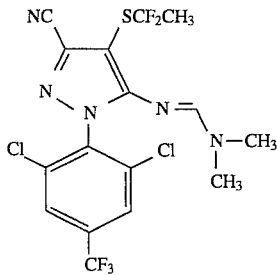

(Process Variant d)

0.4 g (0.001 mol) of 5-amino-3-cyano-4-(1,1-difluoroethylthio)-1-(2,6-dichloro-4-trifluoromethylphenyl)pyrazole in 2 g (0.017 mol) of dimethylformamide dimethyl acetal is heated for 18 hours at 130° C. and subsequently evaporated in vacuo on a rotary evaporator.

0.4 g (89% of theory) of 5-(N,N-dimethylaminomethylideneamino)-3-cyano-4-(1,1-difluoroethylthio)-1-(2,6-dichloro-4-trifluoromethylphenyl)-pyrazole is obtained as an orange oil of boiling point 220° C./0.01 mm.

Example 30

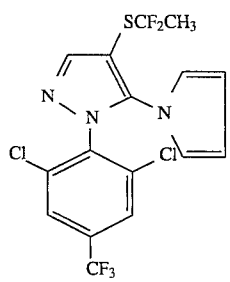

(Process Variant e)

5.88 g (0.015 mol) of 5-amino-4-(1,1-difluoroethylthio)-1-(2,6-dichloro-4-trifluoromethylphenyl)-pyrazole are dissolved in 100 ml of toluene, 2.2 g (0.0165 mol) of 2,5-dimethoxytetrahydrofuran and a spatula-tip full of p-toluenesulphonic acid are added, and the mixture is heated for 20 hours on a water separator. The solvent is stripped off in vacuo, and the residue which remains is stirred with ligroin and filtered off with suction.

4.6 g (69% of theory) of 4-(1,1-difluoroethylthio)-1-(2,6-dichloro-4-trifluoromethylphenyl)-5-(pyrrol-1-yl)pyrazole are obtained.

Example 31

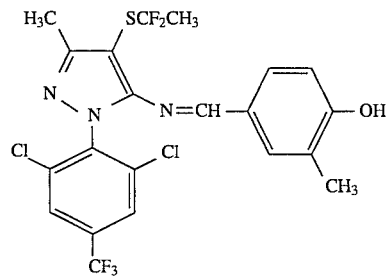

(Process Variant f)

5 g (12.3 mmol) of 5-amino-1-(2,6-dichloro-4-trifluoromethylphenyl)-3-methyl-4-(1,1-difluoroethylthio)-pyrazole and 5 g (32.9 mmol) of 3-methoxy-4-hydroxybenzaldehyde are treated with 4 g of molecular sieve Baylith SV 133 in the absence of a solvent and the mixture is stired for 18 hours at an oil-bath temperature of 140° C. For working-up, the mixture is dissolved in methylene chloride, and the molecular sieve is removed by filtration. The filtrate is concentrated in vacuo, and the excess of vanillin is removed by distillation (up to 140° C./0.1 mm). The brown residue is taken up in ethanol and filtered through 100 g of silica gel 60. After evaporation of the solvent, 2.4 g (36% of theory) of 5-(4-hydroxy-3-methoxybenzylideneamino)-1-(2,6-dichloro-4- trifluoromethylphenyl)-3-methyl-4-(1,1-difluoroethylthio)-pyrazole remain as a shiny brown solid of melting point 67° C.

Example 32

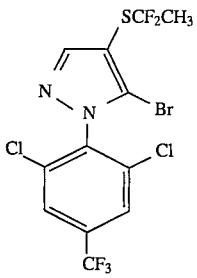

(Process Variant h)

5.88 g (0.015 mol) of 5-amino-4-(1,1-difluoroethylthio)-1-(2,6-dichloro-4-trifluoromethylphenyl)-pyrazole are dissolved in 50 ml of bromoform. 4.64 g (0.045 mol) of tert-butyl nitrite are added dropwise at 80° C. and stirring is subsequently continued for 1 hour at 80° C. The solvent is then stripped off in vacuo.

3.7 g (54% of theory) of 5-bromo-4-(1,1-difluoroethylthio)-1-(2,6-dichloro-4-trifluoromethylphenyl)-pyrazole are obtained. $^1$H-NMR δ*)=7.8 ppm (s, 2H); 7.75 ppm (s, 1H); 1.95 ppm (t, 3H).

Example 33

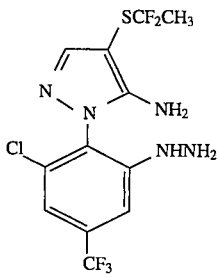

(Process Variant i)

5.88 g (0.015 mol) of 5-amino-4-(1,1-difluoroethylthio)-1-(2,6-dichloro-4-trifluoromethylphenyl)-pyrazole are dissolved in 100 ml of dioxane and refluxed for 24 hours with 1.5 g (0.03 mol) of hydrazine hydrate. After this, a further 1.5 g (0.03 mol) of hydrazine hydrate are added, and refluxing is continued for 24 hours. The solvent is then stripped off in vacuo, the residue is taken up in water, and the mixture is extracted using dichloromethane.

After the dichloromethane has been distilled off in vacuo, 4.1 g (71% of theory) of 5-amino-4-(1,1-difluoroethylthio)-1-(2-chloro-4-trifluoromethyl-6-hydrazinophenyl)-pyrazole of melting point 98°–99° C. are obtained.

Example 34

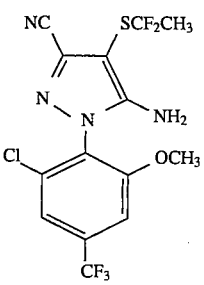

(Process Variant i)

1.3 g (0.003 mol) of 5-amino-3-cyano-4-(1,1-difluoroethylthio)-1-(2,6-dichloro-4-trifluoromethylphenyl)-pyrazole and 0.4 g (0.007 mol) of sodium methylate are refluxed for 6 hours in 20 ml of dry methanol. After this, a further 0.3 g (0.005 mol) of sodium methylate are added, and refluxing is continued for 10 hours. After the solvent has been stripped off in vacuo, the residue which remains is stirred with water and subjected to filtration with suction. The precipitate is washed repeatedly with water and dried.

1.1 g (85% of theory) of 5-amino-3-cyano-4-(1,1-difluoroethylthio)-1-(2-chloro-4-trifluoromethyl-6-methoxyphenyl)-pyrazole of melting point 79° C. are obtained.

Example 35

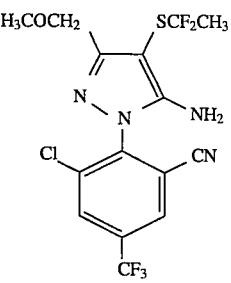

0.7 g (1.7 mmol) of 5-amino-1-(2-chloro-6-fluoro-4-trifluoromethylphenyl)-3-methoxymethyl-4-(1,1-difluoroethylthio)-pyrazole and 1 g (6.54 mmol) of tetraethylammonium cyanide are dissolved in 5 ml of anhydrous dimethylformamide and the mixture is stirred for 18 hours at approximately 100°–110° C. For working-up, the mixture is poured into 100 ml of water, and the solid obtained is filtered off with suction. After the product has been washed repeatedly with water, 0.45 g (63% of theory) of 5-amino-1-(2-chloro-6-cyano-4-trifluoromethyl)-3-methoxymethyl-4-(1,1-difluoroethylthio)-pyrazole is obtained as an ochre solid of melting point 84° C.

Example 36

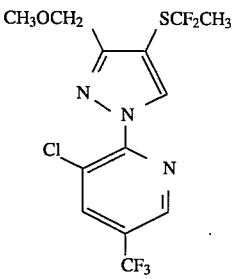

18 ml of water and 18 ml of concentrated sulphuric acid are added at 0° C. to 9 g (0.022 mol) of 5-amino-1-(2-chloro-4-trifluoromethylpyridyl)-3-methoxymethyl-4-(1,1-difluoroethylthio)-pyrazole. A solution of 2.3 g (0.033 mol) of sodium nitrite and 10 ml of water is added dropwise at 0° C. in the course of approximately 30 minutes. After 0.5 g of urea have been added, 27 ml (0.261 mol) of hypophosphorous acid (50% strength aqueous solution) are added dropwise at 0° C. Stirring is then continued for 18 hours at room temperature. After the addition of potassium carbonate, the alkaline solution is extracted using dichloromethane. The combined dichloromethane phases are dried over MgSO₄ and then concentrated in vacuo. The oil which remains is then distilled using a bulb tube. At 180° C./0.1 mm, 4.2 g (48% of theory) of 1-(2-chloro-4-trifluoromethylpyridyl)-3-methoxymethyl-4-(1,1-difluoroethylthio)-pyrazole are obtained as an orange oil.

The following end products of the formula (I) can be obtained analogously to Preparation Examples 28 to 36 and in accordance with the abovementioned processes (c), (d), (e), (f), (g), (h) and (i):

TABLE 3

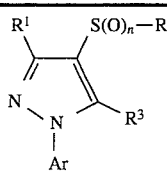

(I)

| Ex. No. | R¹ | R² | R³ | n | Ar | Physical constants |
|---|---|---|---|---|---|---|
| 37 | H | —CF₂CH₃ | NH₂ | 0 | 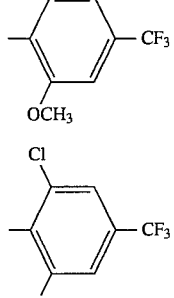 | |
| 38 | CH₃ | —CF₂CH₃ | NH₂ | 0 | 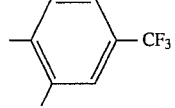 | m.p.: 131–133° C. |
| 39 | —CN | —CF₂CH₃ | —N=CH—N(CH₃)₂ | 0 |  | |
| 40 | CH₃ | —CF₂CH₃ | 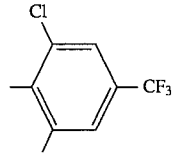 | 0 | 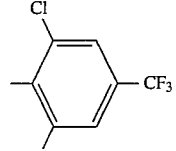 | |
| 41 | CH₃ | —CF₂CH₃ | Br | 0 | 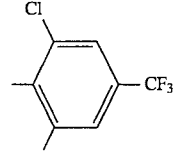 | |
| 42 | H | —CF₂CH₃ | NH₂ | 0 | | |

TABLE 3-continued

Structure (I):
$R^1$ and $S(O)_n-R^2$ on pyrazole, $R^3$ at position 3, N-Ar.

| Ex. No. | R¹ | R² | R³ | n | Ar | Physical constants |
|---|---|---|---|---|---|---|
| 43 | CH₃ | —CF₂CH₃ | NH₂ | 0 | 2,6-di(OCH₃)-4-CF₃-phenyl | m.p.: 135–138° C. |
| 44 | —CH₂OCH₃ | —CF₂CH₃ | NH₂ | 0 | 2,6-diCl-4-CF₃-phenyl | Resin |
| 45 | —CH₂OCH₃ | —CF₃ | NH₂ | 0 | 2-Cl-4-CF₃-6-(NH—NH₂)-phenyl | |
| 46 | —CH₂OCH₃ | —CF₂CH₃ | NH₂ | 0 | 2-Cl-4-CF₃-6-(NH—NH₂)-phenyl | |
| 47 | —CH₃ | —CF₂CH₃ | —N=CH—(4-CF₃-3-OCH₃-phenyl) | 0 | 2,6-diCl-4-CF₃-phenyl | m.p.: 90° C. |
| 48 | —CH₃ | —CF₂CH₃ | —N=CH—(pyridin-3-yl) | 0 | 2,6-diCl-4-CF₃-phenyl | Wax |

Preparation of the Starting Compounds

Example (II-1)

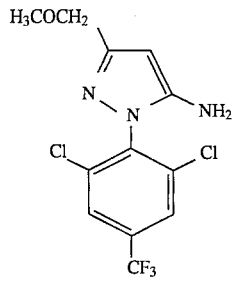

37 g (151 mmol) of 2,6-dichloro-4-trifluoromethylphenylhydrazine and 4.9 g (438 mmol) of 1-cyano-2-amino-3-methoxy-propene are refluxed for 24 hours in 300 ml of ethanol and 20 ml of acetic acid. After this, a further 12 g (49 mmol) of 2,6-dichloro-4-trifluoromethylphenylhydrazine are added, and refluxing is continued for 24 hours. The solvent is subsequently stripped off in vacuo, and the residue is purified by column chromatography (silica gel; eluent: cyclohexane/ethyl ester 1:1).

48.4 g (71% of theory) of 5-amino-1-(2,6-dichloro-4-trifluoromethylphenyl)-3-methoxy-methyl-pyrazole are obtained as an oil.

$^1$H-NMR $\delta^*$)=7.7 ppm (s, 2H); 5.74 ppm (s, 1H); 4.42 ppm (s, 2H); 3.4 ppm (s, 3H).

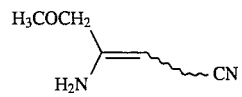

A solution of 15 g (0.21 mol) of methoxyacetonitrile and 10 g (0.24 mol) of acetonitrile in 50 ml of dry tetrahydrofuran is added dropwise in the course of approximately 30 minutes to 21.5 g (0.19 mol) of potassium tert-butylate in 250 ml of dry tetrahydrofuran. After the addition has ended, the mixture is refluxed for a further 24 hours. After carefully hydrolysing with water, the mixture is extracted with dichloromethane. The combined organic phases are dried over magnesium sulphate and then concentrated in vacuo. Subsequent fractional distillation at 80° C./0.2 mm gives 8.9 g (38% of theory) of 2-amino-1-cyano-3-methoxypropene as an orange oil.

The $^{13}$C-NMR data reveal that the ratio of the E/Z isomers is 1:4.

Example (II-2)

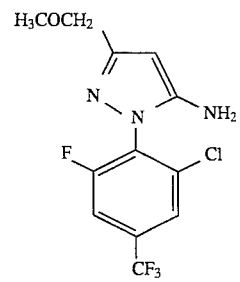

Analogously, 5-amino-1-(2-chloro-6-fluoro-4-trifluoromethylphenyl)-3-methoxymethylpyrazole is obtained from 2-chloro-6-fluoro-4-trifluoromethylphenyl-hydrazine and 2-amino-1-cyano-3-methoxy-propene.

Example (II-3)

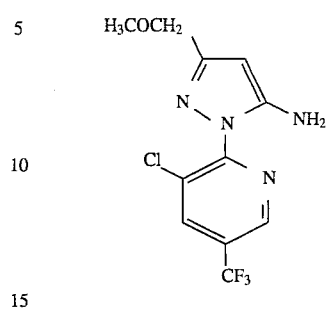

Analogously, 5-amino-1-(2-chloro-4-trifluoromethylpyridyl)-3-methoxymethyl-pyrazole is obtained as an oil from 2-chloro-4-trifluoromethylpyridyl-hydrazine and 2-amino-1-cyano-3-methoxypropene.

$^1$H-NMR $\delta^*$)=8.6 ppm (d, 1H); 8.13 ppm (d, 1H); 5.67 ppm (s, 1H); 4.8 ppm (bs, NH$_2$); 4.41 ppm (s, 2H); 3.4 ppm (s, 3H).

Example (II-4)

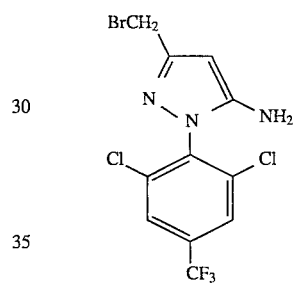

1.5 g (4.4 mmol) of 5-amino-1-(2,6-dichloro-4-trifluoromethylphenyl)-3-methoxymethyl-pyrazole are heated for approximately 8 hours at 120°–130° C. in a mixture of 30 ml of 48% strength HBr and 15 ml of acetic acid. The reaction mixture is concentrated in vacuo and then stirred with dilute ammonia solution. The brown solid is filtered off with suction and repeatedly washed with water.

1.6 g (93% of theory) of 5-amino-1-(2,6-dichloro-4-trifluoromethylphenyl)-3-bromomethylpyrazole of melting point 220° C. are obtained.

Example (II-5)

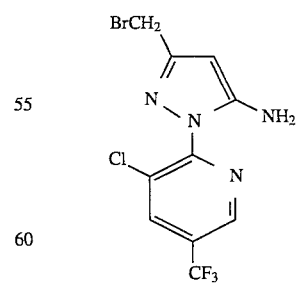

Analogously, 5-amino-1-(2-chloro-4-trifluoromethylpyridyl)-3-bromomethyl-pyrazole is obtained from 5-amino-1-(2-chloro-4-trifluoromethylpyridyl)-3-methoxymethylpyrazole, 48% strength HBr solution and acetic acid.

Example (II-6)

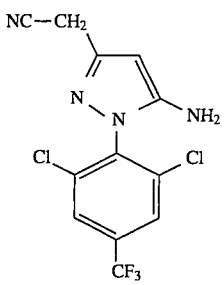

5 g (12.9 mmol) of 5-amino-1-(2,6-dichloro-4-trifluoromethylphenyl)-3-bromomethyl-pyrazole and 2.5 g (51 mmol) of sodium cyanide in 30 ml of water are stirred for 18 hours at 90° C. in the presence of 4 g (17.6 mmol) of triethylbenzylammonium chloride. The mixture is cooled to approximately 5° C., and the grey solid is filtered off with suction. Chromatography on silica gel 60 (eluent:methylene chloride/ethanol 1:1) gives 1.7 g (40% of theory) of 5-amino-1-(2,6-dichloro-4-trifluoromethylphenyl-3-cyanomethyl-pyrazole as a brown solid of melting point 98° C.

*) The $^1$H-NMR spectra were recorded in deuterochloroform (CDCl$_3$) using tetramethylsilane (TMS) as the internal standard. The data given is the chemical shift as δ value in ppm.

**) The $^1$H-NMR spectra were recorded in deuterated dimethyl sulphoxide (CDCl$_3$)$_2$SO) with tetramethylsilane (TMS) as the internal standard. The data given is the chemical shift as δ value in ppm.

Use Examples

In the Use Examples which follow, the compound given below is employed as comparison substance:

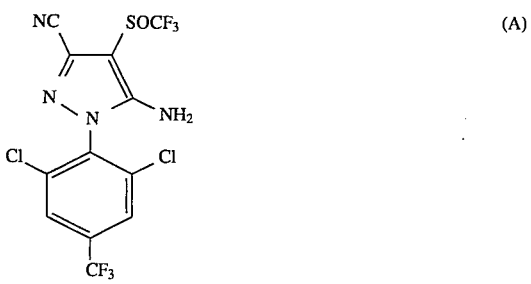

(A)

5-Amino-1- [2,6-dichloro-4-(trifluoromethyl)-phenyl]-4 -[(trimethyl)-sulphinyl]-3-cyano-1H -pyrazole (disclosed in EP-A 295 117)

Example A

Myzus Test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested with the peach aphid (*Myzus persicae*) are treated by being dipped into the preparation of active compound of the desired concentration.

After the specified period of time, the destruction in % is determined. 100% means that all the aphids have been killed; 0% means that none of the aphids have been killed.

In this test, a superior activity compared with the prior art (degree of destruction 0%) is shown, for example, by the compounds of Preparation Examples 1, 6 and 18 with a degree of destruction of between 98% and 100% at a Concentration of active compound of 0.1% after one day.

Example B

Aphis Test (Systemic Action)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Vicia faba*) which are heavily infested with the black bean aphid (*Aphis fabae*) are each watered with 20 ml of preparation of active compound of the desired concentration in such a way that the preparation of active compound penetrates into the soil without wetting the shoot. The active compound is taken up by the roots and passes to the shoot.

After the specified period of time, the destruction in % is determined. 100% means that all the aphids have been killed; 0% means that none of the aphids have been killed.

In this test, a superior activity compared with-the prior art (degree of destruction 0%) is shown, for example, by the compounds of Preparation Examples 1, 6, 18, 21 and 33 with a degree of destruction of between 90% and 100% at a concentration of active compound of 0.02% after four days.

Example C

Critical Concentration Test/Root-Systemic Action.
Test insect: Phaedon cochleariae larvae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is transferred into pots and these are planted with cabbage (*Brassica oleracea*). The active compound can in this way be taken up from the soil by the roots of the plants and be transferred into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, a superior activity compared with the prior art (degree of destruction 0%) is shown, for example, by the compounds of Preparation Examples 1, 6, 15, 25, 33, 37 and 38 with a degree of destruction of in each case 100% at a concentration of active compound of 2.5 ppm.

Example D

Critical Concentration Test/Root-Systemic Action
Test insect: Myzus persicae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is transferred into pots and these are planted with cabbage (*Brassica oleracea*). The active compound can in this way be taken up from the soil by the roots of the plants and be transferred into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, a degree of destruction of 100% compared with the prior art (degree-of destruction 0%) is shown, for example, by the compound of Preparation Example 6 at a concentration of active compound of 20 ppm.

Example E

Blowfly Larvae Test
Test animals: *Lucilia cuprina* larvae
Emulsifier:
  35 parts by weight of ethylene glcyol monomethyl ether
  35 parts by weight of nonylphenol polyglycol ether To produce a suitable preparation of active compound, three parts by weight of active compound are mixed with seven parts by weight of the abovementioned mixture and the emulsion concentrate thus obtained is diluted with water to the particular desired concentration.

About 20 *Lucilia cuprina* res. larvae are introduced into a test tube which contains approx. 1 cm$^3$ of horse meat and 0.5 ml of the preparation of active compound. After 24 hours, the effectiveness of the preparation of active compound is determined. 100% means that all blowfly larvae have been killed; 0% means that none of the blowfly larvae have been killed.

In this test, a destructive activity of 100%. is shown, for example, by the compounds of Preparation Examples 5, 14, 18, 20, 22, 28 and 33 at a concentration of active compound of $\geq$300 ppm, compared with the prior art where this activity is only achieved at a concentration of active compound of 1000 ppm.

Example F

Fly Test
Test animals: *Musca domestica*, strain WHO (N)
Solvent:
  35 parts by weight of ethylene glycol monomethyl ether
  35 parts by weight of nonylphenol polyglycol ether To produce a suitable formulation, three parts by weight of active compound are mixed with seven parts of the abovementioned solvent/emulsifier mixture, and the emulsion concentrate thus obtained is diluted with water to the particular desired concentration.

2 ml of this preparation of active compound are pipetted onto filter paper discs ($\phi$9.5 cm) located in Petri dishes of a suitable size. After the filter paper discs have dried, 25 test animals are introduced into the Petri dish, which is covered.

After 6 hours, the effectiveness of the preparation of active compound is determined. The effectiveness is expressed in %. 100% means that all flies have been killed; 0% means that none of the flies have been killed.

In this test, a superior activity (100% destruction) compared with the prior art (<100%) is shown, for example, by the compound of Preparation Example (6) at a concentration of active compound of 1 ppm.

Example G

Cockroach Test
Test animals: *Blattella germanica* or *Periplaneta americana*
Solvent:
  35 parts by weight of ethylene glycol monomethyl ether
  35 parts by weight of nonylphenol polyglycol ether To produce a suitable formulation, three parts by weight of active compound are mixed with seven parts of the abovementioned solvent/emulsifier mixture, and the emulsion concentrate thus obtained is diluted with water to the particular desired concentration.

2 ml of this preparation of active compound are pipetted onto filter paper discs ($\phi$9.5 cm) located in Petri dishes of a suitable size. After the filter paper discs have dried, 5 test animals (*Blattella germanica* or *Periplaneta americana*) are introduced into the Petri dish, which is covered.

After 6 hours, the effectiveness of the preparation of active compound is determined. The effectiveness is expressed in %. 100% means that all cockroaches have been killed; 0% means that none of the cockroaches have been killed.

In this test, a superior activity (100% destruction at a concentration of active compound of >10 ppm) compared with the prior art (degree of destruction <100% at a concentration of active compound of 10 ppm) is shown, for example, by the compound of Preparation Example (1).

Example H

Flea In-Vitro Test (All Development Stages)
Test subject: All stages (eggs, larvae, pupae and adults) of *Ctenocephalides felis*.
Test procedure:
  Blood meal is dried overnight in a shallow dish at approximately 70° C. and then screened using a mesh size of 0.63 mm.
  1.8 g portions of this prepared blood meal are transferred into plastic Petri dishes of $\phi$9.8 cm.
  Using an Eppendorf pipette, 0.2 ml of substance are placed on the 1.8 g of blood meal (dilution factor 1:10).
  That is to say, at a use concentration of 1 ppm, the aqueous solution must have a concentration of 10 ppm. The solution is distributed dropwise over the entire surface of-the blood meal.
  These prepared dishes are allowed to dry overnight. Using a suitable device, the substance, which is now in the form of dried lumps of blood meal, is crushed and distributed uniformly in the Petri dish by rotating movements. A spatula-full of sieved flea eggs (which are obtained from artificially infected cats) is now added to these prepared test dishes. The dish is sealed with Parafilm and shaken vigorously.

Incubation is effected at 25° C. and the relative atmospheric humidity of 85%. At certain intervals, the dishes are examined for development stages of fleas.

Test criteria: The criteria used for the in-vitro activity of a substance is the inhibition of flea development or a standstill of the development before the adult stage is reached.

Evaluation:

Effective: No adult fleas after 1½ times the development time.

Ineffective: Adult fleas after 1½ times the development time.

In this test, a clearly superior activity (destruction of 100% at an active compound concentration of as little as 1 ppm) compared with the prior art (0% destruction at an active compound concentration of 10%) is shown, for example, by the compound of Preparation Example (5).

It will be understood that the specification and examples are illustrative but not limitative of the present invention and that other embodiments within the spirit and scope of the invention will suggest themselves to those skilled in the art.

What is claimed is:

1. A substituted 1-arylpyrazole of the formula

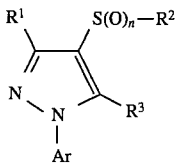

(I)

wherein $R^1$ represents hydrogen, cyano, alkyl, alkoxyalkyl, alkylthioalkyl, halogenoalkyl or cyanoalkyl, $R^2$ represents difluoroethyl or trifluoroethyl, $R^3$ represents hydrogen, amino, halogen or one of the following groups

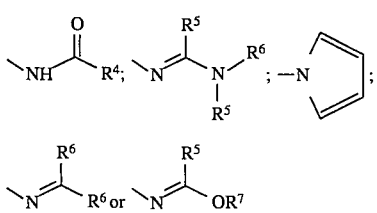

in which $R^4$ represents alkyl, halogenoalkyl, alkoxyalkyl or optionally substituted phenyl, $R^5$ represents hydrogen or alkyl, $R^6$ represents hydrogen, alkyl or optionally substituted phenyl, and $R^7$ represents alkyl, or $R^5$ and $R^6$ together with the carbon atom to which they are bonded represent an optionally substituted heterocycle, Ar represents optionally substituted pyridyl, and n represents a number 0, 1 or 2.

2. A substituted 1-arylpyrazole according to claim 1, wherein $R^1$ represents hydrogen, cyano, ($C_1$-$C_6$)-alkyl, ($C_1$-$C_4$)-alkoxy-($C_1$-$C_4$)-alkyl, ($C_1$-$C_4$)-halogenoalkyl or ($C_1$-$C_2$)-cyanoalkyl, $R^2$ represents difluoroethyl or trifluoroethyl, $R^3$ represents hydrogen, amino, halogen or one of the following groups

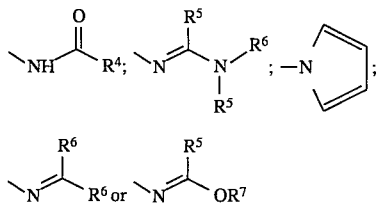

wherein $R^4$ represents ($C_1$-$C_6$)-alkyl, ($C_1$-$C_6$)-halogenoalkyl having 1–3 halogen atoms, ($C_1$-$C_6$)-alkoxy-($C_1$-$C_6$)-alkyl, or phenyl which is optionally monosubstituted to trisubstituted by identical or different substituents, $R^5$ represents hydrogen or ($C_1$-$C_6$)-alkyl, $R^6$ represents hydrogen, ($C_1$-$C_6$)-alkyl, or phenyl which is optionally monosubstituted to trisubstituted by identical or different substituents, $R^7$ represents ($C_1$-$C_6$)-alkyl or $R^5$ and $R^6$ together with the carbon atom to which they are bonded represent optionally substituted pyridyl, Ar represents pyridyl optionally monosubstituted to trisubstituted by identical or different substituents from the series comprising halogen, halogeno ($C_1$-$C_6$)alkyl, halogeno($C_1$-$C_6$)alkylthio, halogeno($C_1$-$C_6$)alkoxy, alkoxy, hydrazino, ($C_1$-$C_6$)-dialkylhydrazino, amino, amino ($C_1$-$C_6$)alkyl, diamino($C_1$-$C_6$)alkyl, imino($C_1$-$C_6$)alkyl, cyano, ($C_1$-$C_6$)alkylthio or the group

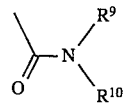

in which $R^9$ and $R^{10}$ are identical or different and represent hydrogen or ($C_1$-$C_6$)-alkyl, and n represents a number 0, 1 or 2.

3. A substituted 1-arylpyrazole according to claim 1, wherein $R^1$ represents hydrogen, cyano, ($C_1$-$C_4$)-alkyl, ($C_1$-$C_4$)-alkoxy-($C_1$-$C_2$)-alkyl, ($C_1$-$C_2$)-halogenoalkyl having 1 to 5 identical or different fluorine, chlorine or bromine atoms, or cyanomethyl, $R^2$ represents difluoroethyl or trifluoroethyl, $R^3$ represents hydrogen, amino, bromine or one of the following groups

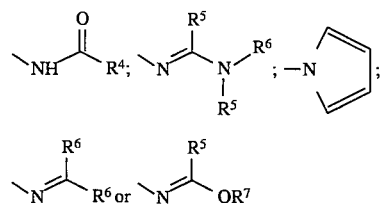

wherein $R^4$ represents ($C_1$-$C_4$)-alkyl, ($C_1$-$C_4$)-halogenoalkyl having 1–3 halogen atoms, ($C_1$-$C_4$)-alkoxy-($C_1$-$C_2$)alkyl, or phenyl which is optionally monosubstituted to trisubstituted by identical or different substituents, $R^5$ represents hydrogen or $(C_1-C_4)$-alkyl, $R^6$ represents hydrogen, $(C_1-C_4)$-alkyl, phenyl which is optionally monosubstituted or disubstituted by identical or different substituents, or 4-hydroxy-3-methoxyphenyl, $R^7$ represents $(C_1-C_4)$-alkyl, or $R^5$ and $R^6$ together with the carbon atom to which they are bonded represent optionally substituted pyridyl, Ar represents pyridyl optionally monosubstituted to trisubstituted by identical or different substituents from the series comprising fluorine, chlorine, trifluoromethyl, trifluoromethylthio, trifluoromethoxy, methoxy, hydrazino, dimethylhydrazino, amino, methylamino, dimethylamino, iminomethyl, cyano, methylthio or the group

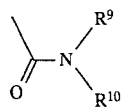

in which $R^9$ and $R^{10}$ are identical or different and represent hydrogen or $(C_1-C_4)$-alkyl, and n represents a number 0, 1 or 2.

4. A substituted 1-arylpyrazole according to claim 1, wherein $R^1$ represents hydrogen, cyano, $(C_1-C_4)$-alkyl, methoxymethyl, ethoxymethyl, methoxyethyl, ethoxyethyl, trifluoromethyl, bromomethyl and cyanomethyl, $R^2$ represents 1,1-difluoroethyl or 2,2,2-trifluoroethyl, $R^3$ represents halogen, amino, bromine or one of the following groups

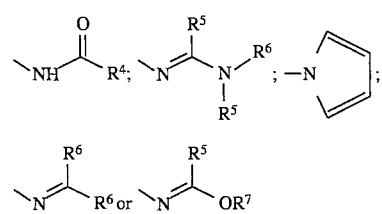

wherein $R^4$ represents $(C_1-C_4)$-alkyl, $(C_1-C_4)$-halogenoalkyl having 1-3 halogen atoms, $(C_1-C_4)$-alkoxy-$(C_1-C_2)$alkyl, or phenyl which is optionally monosubstituted to trisubstituted by identical or different substituents, $R^5$ represents hydrogen or $(C_1-C_4)$-alkyl, $R^6$ represents hydrogen, $(C_1-C_4)$-alkyl, phenyl which is optionally monosubstituted or disubstituted by identical or different substituents, or 4-hydroxy-3-methoxyphenyl, $R^7$ represents $(C_1-C_4)$-alkyl, or $R^5$ and $R^6$ together with the carbon atom to which they are bonded represent optionally substituted pyridyl, Ar represents a 2-pyridyl radical which is substituted in the 4-position by trifluoromethyl and in the 6-position by fluorine or chlorine, and n represents a number 0, 1 or 2.

5. A compound according to claim 1, wherein $R^3$ is amino.

6. A compound according to claim 1, wherein

Ar represents a 2-pyridyl radical which is substituted in the 4-position by trifluoromethyl and in the 6-position by fluorine or chlorine.

7. A compound according to claim 1, wherein such compound is 5-amino-3-methyl-4-(1,1-difluoroethylthio)-1-(3-chloro-5-trifluoromethlpyrid-2-yl)-pyrazole of the formula

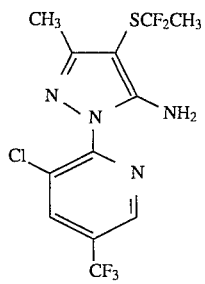

8. An insecticidal composition comprising an insecticidally effective amount of a compound according to claim 1 and a diluent.

9. A method of combating unwanted insects which comprises administering to such insects or to a locus from which it is desired to exclude such insects an insecticidally effective amount of a compound according to claim 1.

10. A substituted 1-arylpyrazole of the formula

wherein $R^1$ represents hydrogen, cyano, alkyl, alkoxyalkyl, alkylthioalkyl, halogenoalkyl or cyanoalkyl, $R^2$ represents difluoroethyl or trifluoroethyl, $R^3$ represents hydrogen, amino, halogen or one of the following groups

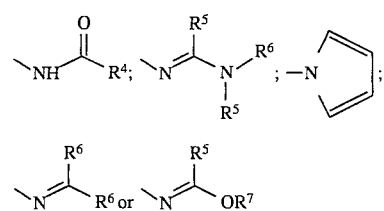

in which $R^4$ represents alkyl, halogenoalkyl, alkoxyalkyl or optionally substituted phenyl, $R^5$ represents hydrogen or alkyl, $R^6$ represents hydrogen, alkyl or optionally substituted phenyl, and $R^7$ represents alkyl, or $R^5$ and $R^6$ together with the carbon atom to which they are bonded represent an optionally substituted heterocycle, Ar represents phenyl which is trisubstituted by identical or different substituents, substituents in the 2-position being fluorine or chlorine, in the 4-position trifluoromethyl and in the 6-position fluorine or chlorine.

11. A compound according to claim 10, wherein $R^1$ represents hydrogen, cyano, $(C_1-C_6)$-alkyl, $(C_1-C_4)$-alkoxy-$(C_1-C_4)$-alkyl, $(C_1-C_4)$-halogenoalkyl or $(C_1-C_2)$-cyanoalkyl, $R^2$ represents difluoroethyl or trifluoroethyl, $R^3$ represents hydrogen, amino, halogen or one of the following groups

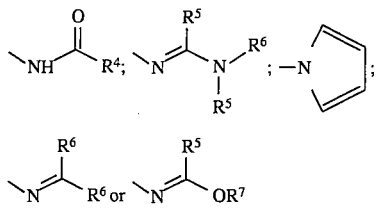

wherein $R^4$ represents $(C_1-C_6)$-alkyl, $(C_1-C_6)$-halogenoalkyl having 1–3 halogen atoms, $(C_1-C_6)$-alkoxy-$(C_1-C_6)$-alkyl, or phenyl which is optionally monosubstituted to trisubstituted by identical or different substituents, $R^5$ represents hydrogen or $(C_1-C_6)$-alkyl, $R^6$ represents hydrogen, $(C_1-C_6)$-alkyl, or phenyl which is optionally monosubstituted to trisubstituted by identical or different substituents, $R^7$ represents $(C_1-C_6)$-alkyl or $R^5$ and $R^6$ together with the carbon atom to which they are bonded represent optionally substituted pyridyl.

12. A compound according to claim 10, wherein $R^3$ is amino.

13. A compound according to claim 10, wherein such compound is 5-amino-3-methyl-4-(1,1-difluoroethylthio)-1-(2,6-dichloro-4-trifluoromethylphenyl)-pyrazole of the formula

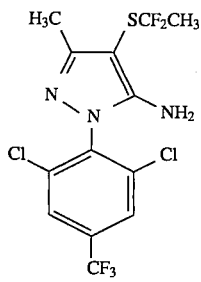

14. A compound according to claim 10, wherein such compound is 5-amino-3-cyano-4-(1,1-difluoroethylthio)-1-(2,6-dichloro-4-trifluoromethylphenyl)-pyrazole of the formula

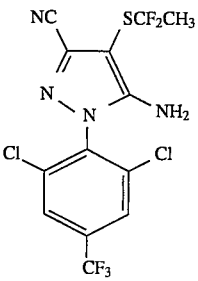

15. A compound according to claim 10, wherein such compound is 5-amino-4-(1,1-difluoroethylthio)-1-(2,6-dichloro-4-trifluoromethylphenyl)-pyrazole of the formula

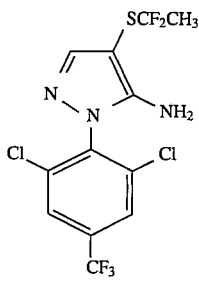

16. A compound according to claim 10, wherein such compound is 5-amino-3-cyano-4-(1,1-difluoroethylthio))-1-(2,4,6-trichlorophenyl)-pyrazole of the formula

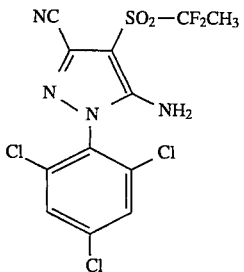

17. An insecticidal composition comprising an insecticidally effective amount of a compound according to claim 10 and a diluent.

18. A method of combating unwanted insects which comprises administering to such insects or to a locus from which it is desired to exclude such insects an insecticidally effective amount of a compound according to claim 10.

19. The method according to claim 18 wherein such compound is 5-amino-3-methyl-4-(1,1-difluorothylthio)-1-(2,6-dichloro-4-trifluoromethylphenyl)-pyrazole, 5-amino-3-cyano-4-(1,1-difluoroethylthio)-1-(2,6-dichloro-4-trifluoromethylphenyl)-pyrazole, 5-amino-4-(1,1-difluoroethylthio)-1-(2,6-dichloro-4-trifluoromethylphenyl)-pyrazole, or 5-amino-3-cyano-4-(1,1-difluoroethylthio))-1-(2,4,6-trichlorophenyl)-pyrazole.

* * * * *

UNITED STATES PATENT AND TRADEMARK OFFICE
CERTIFICATE OF CORRECTION

PATENT NO. : 5,580,843
DATED : December 3, 1996
INVENTOR(S) : Stetter, et al.

It is certified that error appears in the above-indentified patent and that said Letters Patent is hereby corrected as shown below:

Col. 4, line 55    Delete " 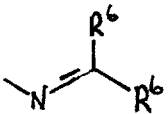 " and substitute

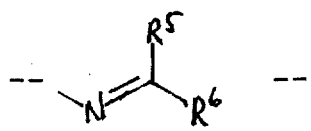

Col. 5, line 42    Delete " 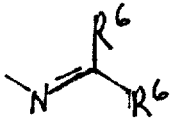 " and substitute

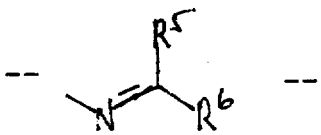

Col. 43, line 42   Delete " 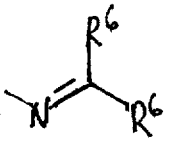 " and substitute

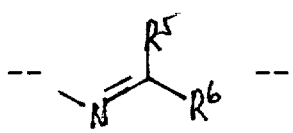

UNITED STATES PATENT AND TRADEMARK OFFICE
CERTIFICATE OF CORRECTION

PATENT NO. : 5,580,843
DATED : December 3, 1996
INVENTOR(S) : Stetter, et al.

It is certified that error appears in the above-indentified patent and that said Letters Patent is hereby corrected as shown below:

Col. 44, line 10    Delete " 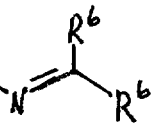 " and substitute

-- 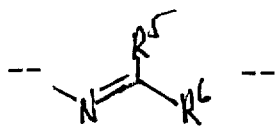 --

Col. 44, line 59    Delete " 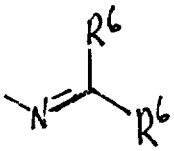 " and substitute

-- 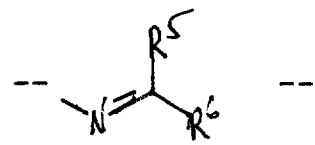 --

Col. 45, line 42    Delete " 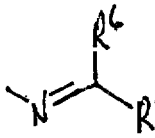 " and substitute

UNITED STATES PATENT AND TRADEMARK OFFICE
CERTIFICATE OF CORRECTION

PATENT NO. : 5,580,843

DATED : December 3, 1996

INVENTOR(S) : Stetter, et al.

It is certified that error appears in the above-indentified patent and that said Letters Patent is hereby corrected as shown below:

Col. 45, line 42 Cont'd -- 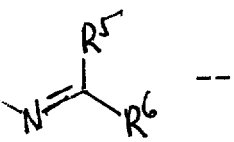 --

Col. 46, line 48   Delete " 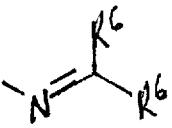 " and substitute

-- 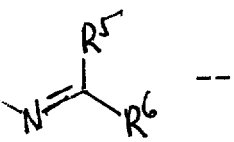 --

Col. 47, line 15   Delete " 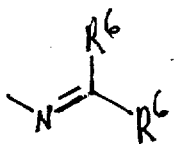 " and substitute

UNITED STATES PATENT AND TRADEMARK OFFICE
CERTIFICATE OF CORRECTION

PATENT NO. : 5,580,843
DATED : December 3, 1996
INVENTOR(S) : Stetter, et al.

It is certified that error appears in the above-indentified patent and that said Letters Patent is hereby corrected as shown below:

Col. 47, line 15 Cont'd -- 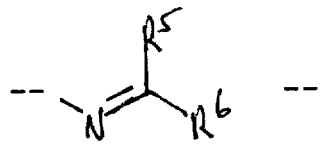 --

Signed and Sealed this

Sixth Day of May, 1997

*Attest:*

BRUCE LEHMAN

*Attesting Officer*  *Commissioner of Patents and Trademarks*